United States Patent [19]

Clift et al.

[11] Patent Number: 4,829,838
[45] Date of Patent: May 16, 1989

[54] METHOD AND APPARATUS FOR THE MEASUREMENT OF THE SIZE OF PARTICLES ENTRAINED IN A GAS

[75] Inventors: Roland Clift, Godalming; Jonathan P. K. Seville, Guildford; Andrew H. J. Take, Rudgwick, all of England

[73] Assignee: National Research Development Corporation, London, England

[21] Appl. No.: 75,901

[22] Filed: Jul. 20, 1987

[30] Foreign Application Priority Data

Jul. 18, 1986 [GB] United Kingdom ............... 8617568

[51] Int. Cl.$^4$ ..................... G01N 15/02; G01N 15/14
[52] U.S. Cl. .................................... 73/865.5; 356/336
[58] Field of Search ....................... 73/865.5; 364/555; 250/222.2; 356/335, 336

[56] References Cited

U.S. PATENT DOCUMENTS

| 3,983,743 | 10/1976 | Olin et al. ............................. 73/28 |
| 4,381,674 | 5/1983 | Abts ................................ 73/865.5 X |
| 4,412,451 | 11/1983 | Uusitalo et al. .................... 73/865.5 |
| 4,613,938 | 9/1986 | Hansen et al. ................. 73/170 R X |
| 4,633,714 | 1/1987 | Mazumder et al. ........... 73/865.5 X |

Primary Examiner—Tom Noland
Attorney, Agent, or Firm—Cushman, Darby & Cushman

[57] ABSTRACT

Apparatus for measuring the size of particles entrained in a gas comprises an optical fibre probe having a hemispherical end and insertable into a stream of gas bearing entrained particles to create a stagnation point in the flowing gas, a Doppler anemometer to measure particle velocity at a point upstream of the stagnation point and a computer-controlled burst counter to determine from the particle velocity measurements the distribution by number of aerodynamic diameter of the particles.

8 Claims, 5 Drawing Sheets $U_\infty = 0.5 ms^{-1}$ $U_\infty = 1.5 ms^{-1}$

METHOD AND APPARATUS FOR THE MEASUREMENT OF THE SIZE OF PARTICLES ENTRAINED IN A GAS

BACKGROUND OF THE INVENTION

This invention relates to methods and apparatus for the measurement of the size of particles entrained in a gas. An existing method is to sample the particles from the gas, for subsequent offline analysis. In addition to the difficulty of ensuring that samples are representative of the entrained particulate, it is then necessary to ensure that the particles measured are no more or less agglomerated than those in the gas. The uncertainties associated with these measurements introduce doubts into measurements of the apparent efficiency of gas cleaning devices. It is therefore desirable to measure the concentration and size distribution of the entrained particles directly in situ without sampling. It is also desirable for the measurement device to be capable of being traversed, so as to obtain representative mean values across a large gas duct.

The "size" of a non-spherical particle can be defined in a variety of different ways. For gas cleaning operations, the parameter of most relevance is usually the Stokes diameter, which describes both the intertial and settling behavior of a particle. It is possible, and sometimes preferable, to infer the Stokes diameter from simple off-line measurements such as are obtained by Coulter Counter or image analysis. The Coulter Counter, for example, measures directly the particle volume and, for wide ranges of particle shape, the volume-equivalent diameter is close to the Stokes diameter. However, these indirect measurements are always time-consuming, demand redispersion in a liquid, and require at least two different methods to be used on the same sample in order to infer the precise relationship between the volume-equivalent and Stokes diameters.

Of the devices currently available for direct measurement of Stokes diameter, horizontal, vertical and centrifugal settling devices are of considerable interest for calibration of other aerodynamic instruments. However, they are essentially laboratory techniques which operate on batch samples and which require experience, care and patience to obtain reliable results. Inertial impaction is probably the commonest industrial technique for measurement of Stokes diameter. However, in addition to requiring the gas to be sampled, inertial impaction measurements are subject to uncertainties arising from the possibilities that particles may bounce or blow off from the impaction plates and that agglomerates may break up on impact. Cyclones with sharp cut-off have been used for particle size measurement. Recently an automated 3-cyclone train has been described using an oscillating microbalance to indicate the masses of particles collected. Although this device is automated, it remains a sampling instrument which gives readings in a few wide size ranges at intervals of tens of seconds.

The TSI "Aerodynamic Particle Sizer" or APS is another relatively new instrument which differs from the other devices in measuring the inertial behavior of individual particles. In principle, it can give finer resolution of the particle size distribution than a device such as a cascade impactor which sorts particles into a few discrete bands. Dilute particle-laden gas is accelerated through a nozzle, so that the entrained particles reach a velocity significantly less than that of the gas. Thus, for each particle, the slip velocity relative to the gas depends upon its inertia, i.e. upon its aerodynamic diameter. The velocities of particles issuing from the nozzle were measured by laser-Doppler anemometry, but the commercial instrument measures the time-of flight between two laser beams separated by 120 m. The particle size distribution is built up from measurements of individual particles. In theory this technique should be absolute, but in practice it is necessary to calibrate the instrument using particles of known aerodynamic diameter. While the APS appears to give reliable measurements for spherical particles, there is some evidence that it undersizes irregular particles. Particle orientation effects are insufficient to explain the discrepancy; A contributory cause may be shape features which induce boundary layer separation at relatively low Reynolds numbers and hence have a strong effect on drag. The APS also has the disadvantage that it is another sampling instrument, with a low sample gas rate which would have to be cooled before being passed to the instrument. Like all single-particle counters, it is subject to "coincidence errors", arising from particles whose times-of-flight overlap, so that most gases of industrial interest also have to be diluted before analysis.

SUMMARY OF THE INVENTION

We have devised an alternative apparatus and method in order to avoid the need to draw a sample. Flowing gas approaches an obstacle in the duct. The gas velocity on the stagnation streamline, u, drops to zero at the stagnation point. The velocity of a particle on the stagnation streamline, v, also falls but, because of the inertia of the particle, it will not follow u. The extent of the difference between v and u increases with increasing particle inertia. Thus the principle on which the present invention is based is to insert a probe into the gas flow, and to measure the velocities of individual particles at a known distance from the stagnation point.

According to the present invention there is provided an apparatus for measuring the size of particles entrained in a gas comprising probe means insertable into a stream of gas bearing entrained particles for creating a stagnation point in said flowing gas, measuring means for measuring particle velocity at a point upstream of said stagnation point and computer means for determining from said particle velocity measurements the distribution by number of aerodynamic diameter of said particles.

BRIEF DESCRIPTION OF THE DRAWINGS

An embodiment of the invention will now be described by way of example with reference to the accompanying drawings in which.

DETAILED DESCRIPTION OF THE PREFERRED EMBODIMENT

Figure 1:
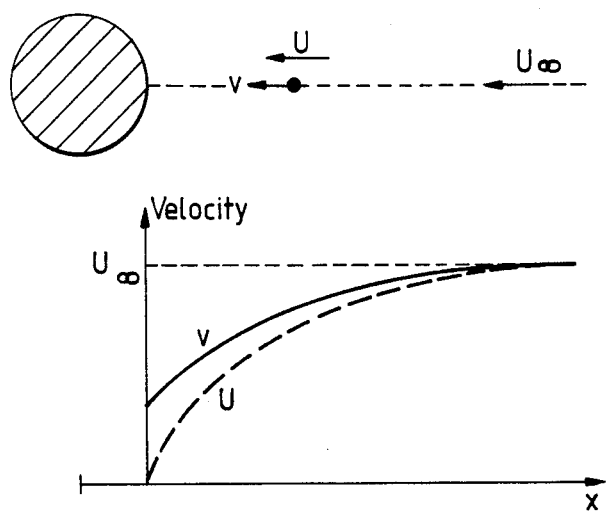
FIG. 1 illustrates gas and particle motion approaching stagnation point of a bluff body.

In this specification, means ascribed to symbols are:
a: Radius of hemispherical probe
$C_D$: Fluid-particle drag coefficient
Cs: Slip correction factor
d: Particle diameter
$d_a$: Aerodynamic particle diameter
$d_e$: Volume-equivalent particle diameter
$d_s$: Stokes diameter of entrained particle
$F_b$: Body force on particle
$F_d$: Fluid-particle interaction force.
St: Stokes number, defined by equation (2)
t: Time
t': Dimensionless time
$u_,$: Local gas velocity
u': Dimensionless gas velocity
u: Approach gas velocity
V: Volume of particle
$v_,$: Particle velocity
x: Coordinate of particle center
x': Dimensionless particle coordinate
$\mu$: Gas viscosity
$\rho$: Gas density
$\rho_p$: Particle density
$\rho_p'$: "Standard" particle density Consider a rigid particle of volume V moving at instantaneous velocity V through a fluid (FIG. 1). In general, the equation of motion of the particle takes the form $$\rho_p V = \frac{dv}{dt} = F_d + F_b \qquad (1)$$

where $\rho_p$ is the particle density and $F_d$ and $F_b$ are the forces acting on the particle, $F_d$ being the instantaneous force exerted on the particle by the fluid and $F_b$ representing body forces due, for example, to gravity or an electric field. The fluid/particle interaction term $F_d$ includes, in general, the force arising from pressure gradients in the fluid and also the drag of the fluid on the particle which depends, in turn, on the velocity of the particle relative to the surrounding fluid and in its present and past acceleration relative to the fluid. For particles in gases, it is usually sufficiently accurate to approximate Fd by the force arising in steady relative motion at the instantaneous slip velocity, $$\text{i.e. } F_d = \frac{n\rho d^2 C_D (u-v) |u-v|}{8 C_s} \qquad (2)$$

wherre u is the gas velocity in the vicinity of the particle, so that (u−v) is the instantaneous slip velocity, d is the particle diameter discussed below, n is the number of particles, and $\rho$ is the gas density. The dimensionless coefficient $C_s$ in equation (2) is the Cunningham "slip correction" factor which allows for the reduction in drag when the particle diameter is of comparable magnitude to the mean free path of molecules in the gas. For particles greater than 1 $\mu$m in size in gases, it is close to unity. The dimensionless drag coefficient $C_D$ is in general a function of the particle Reynolds number:

$$Re_p = |u-v|\rho d/\mu \qquad (3)$$

where $\mu$ is the gas viscosity. Various empirical and semi-empirical relationships for $C_D(Re_p)$ are available.

For $Re_p < 0.5$, and $\bar{n}$ being the average number of particles in a standard unit of volume the relationship can be approximated by Stokes' law:

$$F_d = 3\bar{n}\mu d(u-v)/C_s \qquad (4)$$

The body force term, $F_b$, can be neglected for small particles in rapidly accelerating or decelerating gases, and for flows in which gravity is the only body force, u is horizontal, and the linear drag relationship of equation (4) applies.

All the above simplifications can be applied, at least for an initial analysis, to the in-duct particle sizer. Equation (1) then becomes $$\rho_p V \frac{dv}{dt} = 3\bar{n}\mu d(u-v) \qquad (5)$$

or $$\frac{\rho_p d_e^3}{18 d} \frac{dv}{dt} = u - v \qquad (6)$$

where $d_e$ is the volume-equivalent diameter of the particle, given by $$V = \pi d_e^3/d \qquad (7)$$

Equation (5) shows that d is to be interpreted as the diameter of the sphere which experiences the same fluid drag as the particle. Equation (6) shows that the Stokes diameter of the particle, $d_s$, i.e. the diameter of the sphere with the same inertial behavior, is given by $$d_s^2 = d_e^3/d \qquad (8)$$

The Stokes diameter also corresponds to the diameter of the sphere with the same settling velocity. The aerodynamic diameter $d_a$ is usually defined as the diameter of a sphere of arbitrary standard density $\rho_p'$ with the same settling or inertial behavior as the particle in question. From equation (6), $$d_a = d_s \sqrt{\rho_p/\rho'_p} \qquad (9)$$

In terms of the Stokes diameter, equation (6) becomes $$\frac{\rho_p d_s^2}{18\mu} \frac{d^2 x}{dt^2} = u - \frac{dx}{dt} \qquad (10)$$

where x is the position of the particle. For one-dimensional motion, as on a straight stagnation stream line, x and u can be written as scalars. The resulting equation can be written in dimensionless form by substituting:

$$x' = x/a; \ u' = u/u_\infty; \ t' = u_\infty t/a \qquad (11)$$

where a is the radius of the axi-symmetric body on which the stagnation point occurs, and $u_\infty$ is the velocity of the approach gas flow at large distances from the body. Equation (10) then becomes $$St \frac{d^2 x'}{dt'^2} + \frac{dx'}{dt} = u' \qquad (12)$$

where St is the Stokes number of the particle:

$$St = d_s^2 \tag{13}$$

Equation (12) is the dimensionless form of the simplified equation of motion of the particle. Its solution depends on u', which describes the gas velocity approaching the stagnation point and therefore depends on the shape and Reynolds number of the body, $2u_\infty pa/\mu$. For the in-duct particle sizer, it is convenient to make the upstream surface of the probe in the form of a hemisphere. Provided that the probe Reynolds number is large, the flow around this surface can be represented by flow of an incompressible inviscid fluid around the upstream half of a sphere. The fluid velocity on the stagnation streamline is then given by $$u' = x'^{-3} \tag{14}$$

so that equation (13) becomes $$St \frac{d^2 x'}{dt'^2} + \frac{dx'}{dt'} = \frac{1}{x'^3} - 1 \tag{15}$$

Equation (15) can be solved numerically, for different values of St, given an appropriate initial condition. The true initial condition is $t' = 0$, $x' = \infty$, $dx'/dt' = -1$.

In equation (12) x' is the dimensionless position of the particle, t' is a dimensionless time, and u' is a dimensionless velocity:

$$x' = x/a;\ u' = u/u;\ t' = ut/a \tag{16}$$

where u is the gas velocity at position x on the stagnation streamline.

Figure 2:
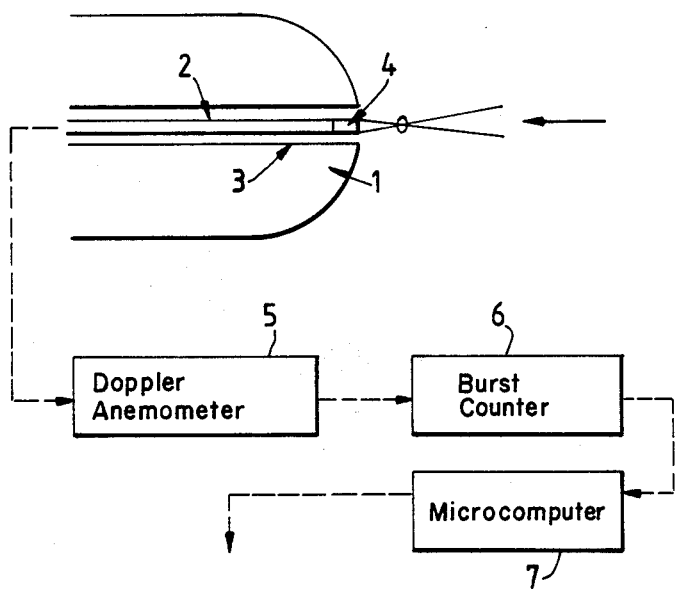
FIG. 2 is a schematic view of an apparatus for measuring particle velocity in accordance with an embodiment of the invention.

The theoretical response of the in-duct particle sizer can be calculated from equation (1) if u' is known as a function of x'. This requires the upstream face of the probe to be designed to a shape for which a theoretical expression for u' is available. For this reason, and also for relative ease of fabrication, the probe has been designed to have a hemispherical end, as shown schematically in FIG. 2. An optical fiber 2 is mounted in a pitot channel 3 and is equipped with a lens 4 focused upstream of the probe end 1. A Doppler anemometer 5 is coupled to the optical fiber 2 and feeds a burst counter 6 which is, in turn monitored by a microcomputer 7 to determine the distribution of the aerodynamic diameter of the particles. The appropriate value for a is then the radius of the hemispherical end and cylindrical probe stem, and x is measured from the center of the hemisphere. Using the appropriate expression for u' the dimensionless particle velocity $$dx'/dt' = v/u_\infty$$

can be calculated, where v = dx/dt is the dimensional particle velocity. The results are shown in dimensionless form in FIG. 3, each curve referring to one value of the particle Stokes number.

Figure 3:
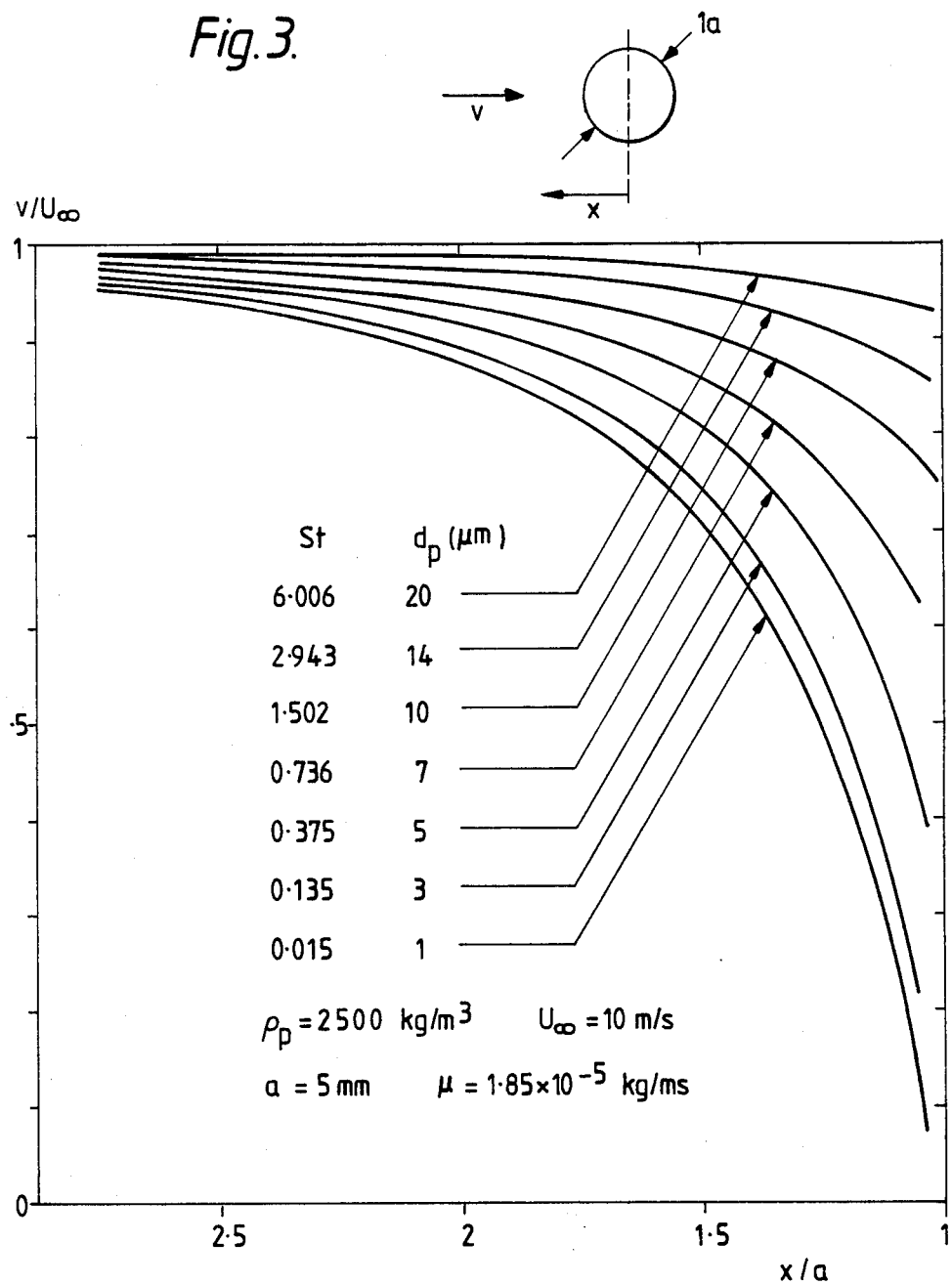
FIG. 3 is a graphical representation of the predicted velocities of particles entrained in a gas approaching a sphere.

FIG. 3 can now be used to select an appropriate probe size, for the approach gas velocity and range of particle sizes of interest. Consider, for example, a gas velocity, $u_\infty$, of 10 ms$^{-1}$ with particles from 1 to 20 $\mu$m to be measured. If the probe radius, a, is designed to be 5 mm, then this range of particle size covers the range of Stokes numbers in FIG. 3. Because the approach velocities are well discriminated, it should be possible to distinguish between sizes in this range by measuring their velocities approaching the stagnation point. It remains to select the position at which the particle velocities are best sensed.

Figure 4:
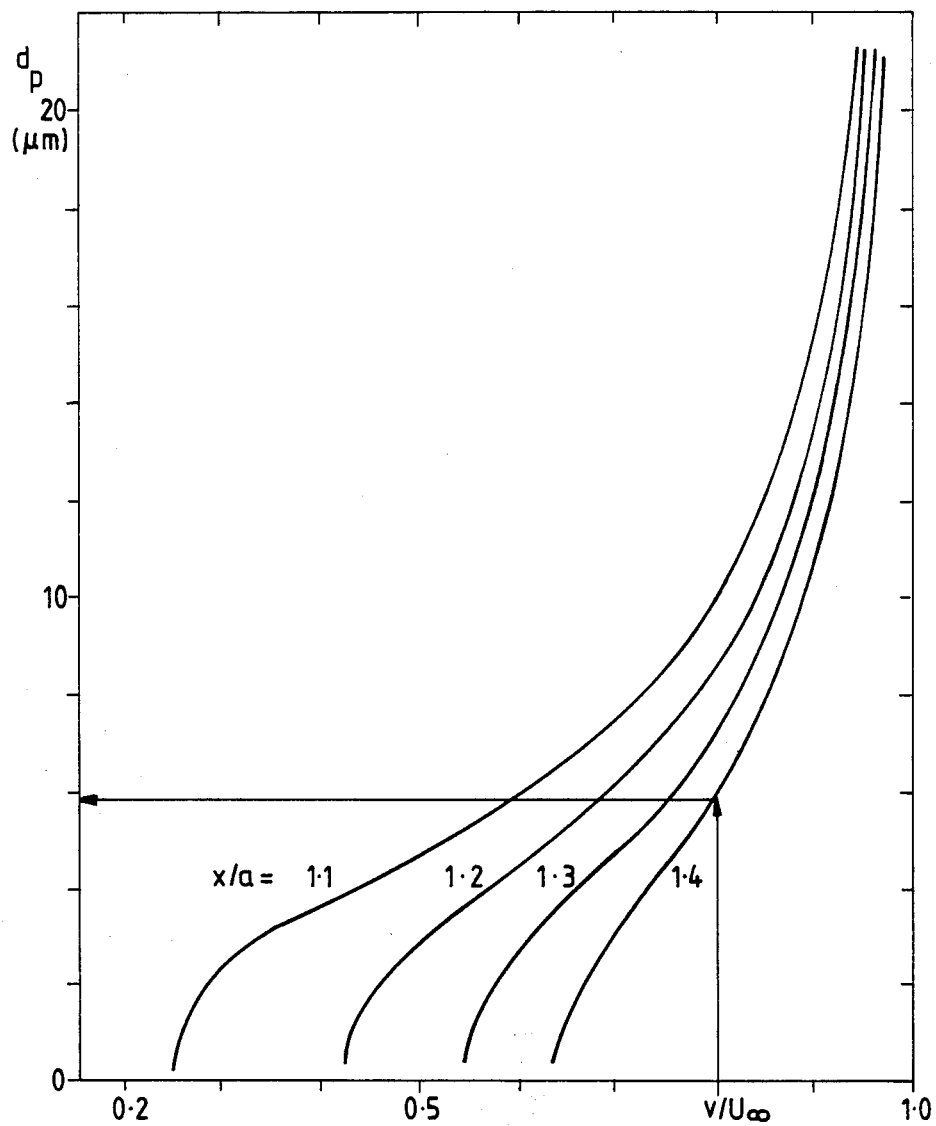
FIG. 4 is a correlation chart.

FIG. 4 shows the same predictions plotted to give particle diameter as a function of $v/u_\infty$ for several measuring positions, x/a. This "calibration chart" clearly shows that maximum resolution should be achieved by measuring particle velocity as close as possible to the surface of the probe, subject to the constraint that the measuring point must be outside the boundary layer. FIG. 4 shows that a suitable measurement position is x/a = 1.1, i.e. 0.5 mm from the surface for a probe tip radius of 5 mm. Furthermore, measurement of velocity with a single probe size cannot discriminate particles over the whole size range, because particles with St greater that about 6 ($d_s = 20$ $\mu$m for these conditions) have such high inertia that their velocity changes little, while for St less than about 0.06 (ds $\approx$ 2 $\mu$m in this case) the particle velocity is barely distinguishable from that of the gas. Thus the measuring range of the device is limited to rough a ten-fold range of particle diameter. However, the range can readily be changed by changing a; i.e. by changing the probe diameter or by using several hemispherical ends of different diameters.

Conveniently, measurements may be made using optic fibers with illumination by a standard 4 mW He-Ne laser which generates polarized light at a wavelength of 633 nm and at a power of 2 mW launched into the fiber. The signals detected can be collected and displayed for inspection by a Gould 4035 digital storage oscilloscope, with suitable traces output off-line to a conventional pen recorder.

Alternative optical fiber systems may be used. In order to compare the performance of different fiber and lens systems, the preliminary tests used as "targets" a number of glass fibers of different sizes mounted on the cone of a 100 mm diameter loudspeaker driven at 1 kHz with amplitude of order 5 mm. This controlled sinusoidal motion of the target should produce Doppler signal bursts related to the driving waveform. A micro-positioner was used to locate the end of the optic fiber precisely relative to the end of the target fiber.

Figure 5A:
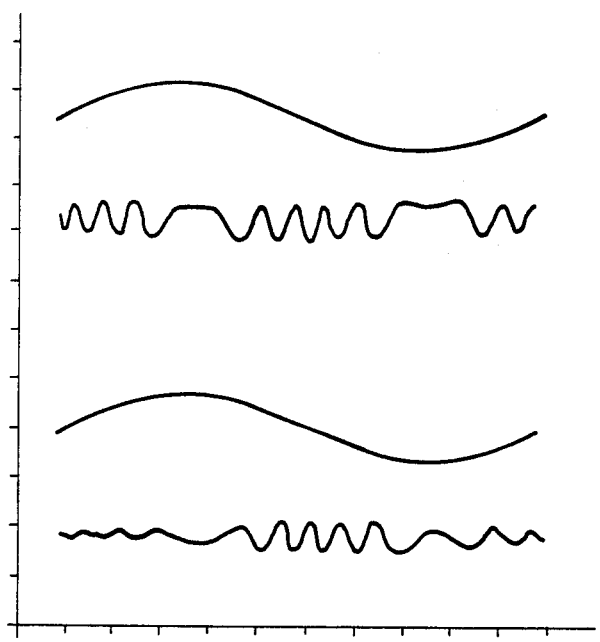
FIGS. 5a and 5b are doppler signals obtained from glass fibers on a loudspeaker.
Figure 5B:
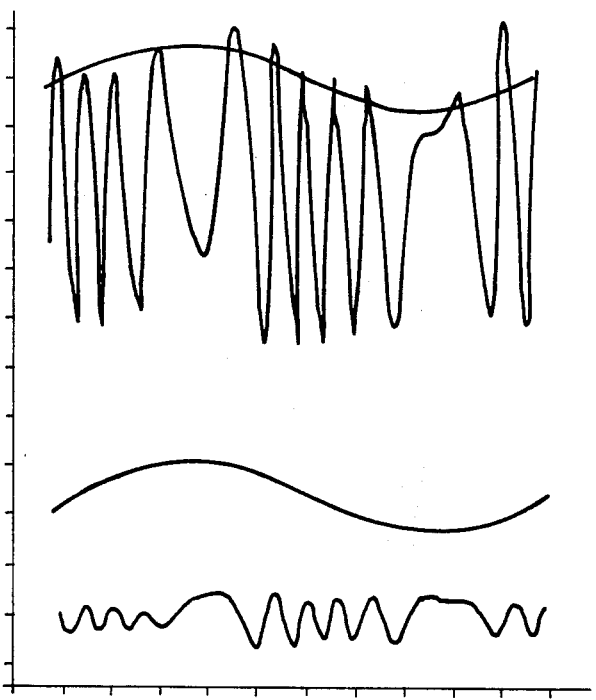

One form of fiber optic Doppler anemometer uses a graded-index glass optical fiber of 100 $\mu$m nominal diameter. FIG. 5a shows traces obtained from the end of a glass fiber of 10 $\mu$m diameter using the standard optic fiber with no lens system at the detection end. The upper trace shows the displacement of the loudspeaker; thus the Doppler signals have the expected form, with high frequency when the target velocity is high. However, some high-frequency noise is apparent, especially in the lower velocity sections. Other systems were therefore tested in an attempt to increase signal strength and reduce noise. The signal was found to be improved significantly by reducing the optical fiber diameter, possibly because multimode fibers were used rather than monomode fibers and reducing the fiber diameter reduces the number of modes by which the fiber transmits the light. Adding a lens to the end of the fiber focusses the illuminating light into a small volume from which scattered light can be received. It was found that, when lenses were used, the signal was still further improved especially when detecting small diameter targets, probably because the focused scattering volume is smaller. The best results were obtained with a SELFOC graded-index cylindrical lens. FIG. 5b shows signals obtained for the 10 $\mu$m target with a SELFOC lens on the end of a 50 μm graded-index glass fiber. The signal strength is seen to be greater. It is strongest when the target is at the focus of the laser light, about 1 mm from the end of the optic head, and weaker at other positions. Qualitatively, this is the type of response required for the in-duct particle sizer.

Figure 6:
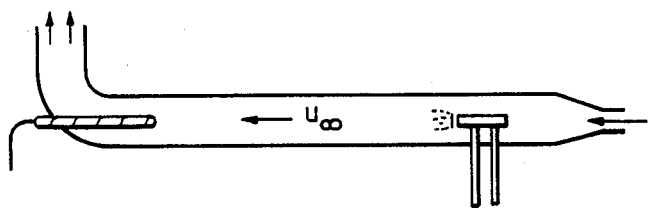
FIG. 6 is a diagram of an apparatus used for in-duct particle size measurement.
Figure 7A:
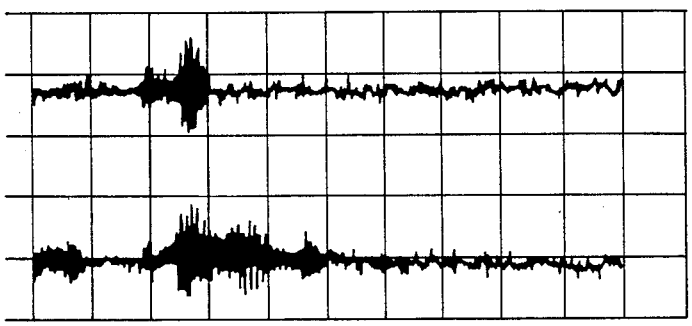
FIGS. 7a to 7c are Doppler traces obtained using the apparatus of FIG. 6.
Figure 7B:
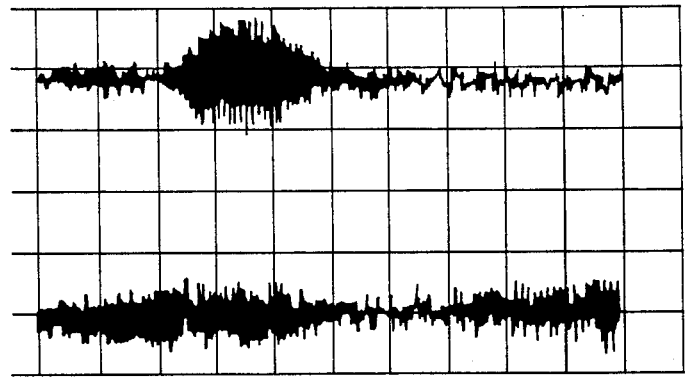
Figure 7C:
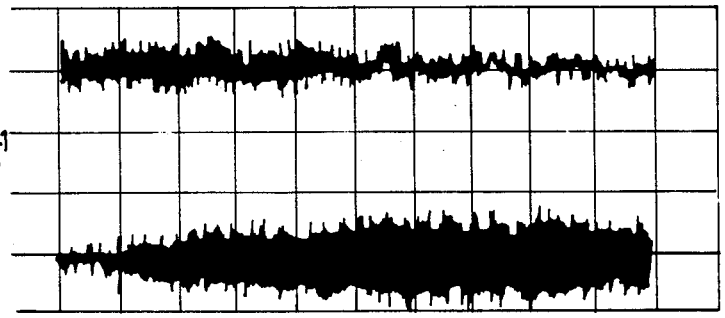

Once it was established that Doppler bursts suitable for further processing can be obtained from a moving target at the required position, further tests were carried out for dispersed particles using the fiber and lens in FIG. 5b. The optic head, without the rest of the probe, was mounted as shown schematically in FIG. 6, facing upstream in a horizontal duct. Air velocities of 0.5, 1.0 and 1.5 m.s.$^{-1}$ were used as the approach flow for these tests, because higher velocities would give rise to Doppler frequencies too high to be stored by the particular digital oscilloscope available. The test particles used were 19.1 μm latex spheres, dispersed into the air flow using a two-fluid atomizer using high pressure air as the driving fluid. No particular measures were taken to ensure that the latex was dispersed as individual particles. Approximating the end of the optic head as a hemisphere of 3 mm radius, the values of St for the 19.1 μm primary particles at the three air velocities are 0.19, 0.38 and 0.58. Referring to FIG. 3, the tests are therefore in the range where slip between the gas and particles should be measurable and dependent on particle size. FIGS. 7b, c and d show typical Doppler "bursts" obtained from entrained particles at these three velocities; clearly these have exactly the form expected. In some traces it is possible to detect a reduction of the Doppler frequency, i.e. deceleration of the particle, through the "burst" as the particle approaches the stagnation point on the optic head. The signals obtained at each air velocity indicate a range of particle velocities, the lowest being close to the value predicted from FIG. 3. Possibly the higher velocities correspond to incompletely dispersed particles, but this remains to be confirmed. Preliminary tests with smaller latex particles confirmed that lower approach velocities were measured.

We claim:

1. Apparatus for measuring the size of particles entrained in a gas comprising probe means insertable into a stream of gas bearing entrained particles to create a stagnation point in said flowing gas, measuring means to measure particle velocity at a point upstream of said stagnation point and computer means to determine from said particle velocity measurements the distribution of the aerodynamic diameter of said particles.

2. Apparatus for measuring the size of particles entrained in a gas as claimed in claim 1 wherein said probe means comprises an optical fiber.

3. Apparatus for measuring the size of particles entrained in a gas as claimed in claim 2 wherein said optical fiber is equipped with a lens focused upstream of the probe means.

4. Apparatus for measuring the size of particles entrained in a gas as claimed in claim 3 wherein a Doppler anemometer is coupled to said optical fiber.

5. Apparatus for measuring the size of particles entrained in a gas as claimed in claim 2 wherein a Doppler anemometer is coupled to said optical fiber.

6. Apparatus for measuring the size of particles entrained in a gas as claimed in claim 2 wherein said optical fiber is a graded index optical fiber.

7. Apparatus for measuring the size of particles entrained in a gas as claimed in claim 1 wherein a diameter of said probe means is varied in order to measure different sizes of particles.

8. A method of measuring the size of particles entrained in a gas comprising inserting probe means into a gas stream bearing entrained particles to create a stagnation point, measuring the particle velocity at a point upstream of said stagnation point and computing from said particle measurements the distribution of the aerodynamic diameter of said particles.

* * * * *